United States Patent [19]

Maihofer

[11] Patent Number: 5,609,830
[45] Date of Patent: Mar. 11, 1997

[54] METHOD AND APPARATUS FOR THE STERILIZATION OF REFUSE, IN PARTICULAR HOSPITAL REFUSE

[75] Inventor: Willi Maihofer, Balingen/Weilstetten, Germany

[73] Assignee: Nordpunkt AG, Novaggio/Ti., Switzerland

[21] Appl. No.: 202,600

[22] Filed: Feb. 28, 1994

Related U.S. Application Data

[62] Division of Ser. No. 37,513, Mar. 22, 1993, abandoned, which is a continuation of Ser. No. 555,003, Jul. 20, 1990, abandoned.

[30] Foreign Application Priority Data

Jul. 26, 1990 [DE]  Germany ........................... 39 24 744.9

[51] Int. Cl.⁶ ........................ A61L 2/12; A61L 2/20
[52] U.S. Cl. .......................... 422/112; 422/21; 422/28; 422/32; 422/27; 422/297; 422/305
[58] Field of Search ................... 422/26, 27, 28, 422/32, 297, 21, 305, 108, 112, 111; 423/DIG. 18

[56] References Cited

U.S. PATENT DOCUMENTS

| | | |
|---|---|---|
| 3,939,287 | 2/1976 | Orwig et al. . |
| 4,015,935 | 4/1977 | Andersson et al. . |
| 4,073,663 | 2/1978 | Lundgren . |
| 5,122,633 | 6/1992 | Moshammer et al. . |

FOREIGN PATENT DOCUMENTS

| | | |
|---|---|---|
| 2908086 | 9/1980 | Germany . |
| 3317300 | 11/1984 | Germany . |
| 3710156 | 10/1988 | Germany . |

Primary Examiner—Timothy McMahon
Attorney, Agent, or Firm—Nikaido Marmelstein Murray & Oram LLP

[57] ABSTRACT

A method and an apparatus for the sterilization of refuse, in particular hospital refuse, is described, according to which plastic containers filled with the refuse are first introduced into a lock chamber in which a preparatory conveyor belt is arranged and thereafter the entire charge of the lock chamber is transferred to a sterilization chamber in which a main conveyor belt is arranged. The sterilization chamber is then hermetically sealed and injection needles are stuck into the respective containers to inject water and/or disinfectant into the interior of the respective plastic containers. The refuse is then treated with microwave energy and subsequently the charge in the sterilization chamber discharged via the discharge opening. With the method and the apparatus according to the invention it is always ensured that the refuse in the interior of the plastic containers is impregnated in adequate manner with water or a disinfectant, this being done before or during the microwave irradiation.

28 Claims, 4 Drawing Sheets

METHOD AND APPARATUS FOR THE STERILIZATION OF REFUSE, IN PARTICULAR HOSPITAL REFUSE

This is a division, of application Ser. No. 08/037,513 filed Mar. 22, 1993 now abandoned, which in turn is a continuation of application Ser. No. 07/555,003, filed Jul. 20, 1990, now abandoned.

BACKGROUND OF THE INVENTION

1. Field of the Invention

The invention relates to a method and apparatus for sterilizing refuse, in particular hospital refuse, using a plurality of disposable refuse containers which after loading with refuse are hermetically sealed by a cover and then introduced preferably severally into a sterilization tunnel and thereafter irradiated with microwaves, water or a disinfectant being introduced into the refuse of the refuse containers either before or during the microwave irradiation and the refuse container or containers then being discharged at a discharge end from the sterilization tunnel.

2. Description of the Prior Art

De-OS 3,317,300 discloses a container for receiving infected refuse, in particular hospital waste. To prevent infections said refuse is sterilized with the aid of microwaves, this being possible because the externally sealable container consists of a material through which microwaves can pass. Said container is equipped in its interior with an insertable and sealable disposable inner container for the infected refuse which consists of a substantially moisture-tight nontearable material which however allows steam and/or microwaves to pass. The outer container of this arrangement can be constructed as pressurized container.

At the inner side of the cover of said inner container a bag or the like containing liquid, preferably disinfectant, may be attached. During the microwave treatment the liquid in the interior of the bag is heated, partially vaporizes and thereby finally causes the bag to burst, the content thereof being emptied into the surrounding refuse.

EP 0 049 430 discloses a bulk material container having a cover, preferably for use as disposable transport vessel, which can also be used for receiving hospital waste.

DE-OS 2,908,086 discloses a method for disinfecting and sterilizing articles infected with germs, said method residing in that in the space surrounding the article to be treated a disinfectant is atomized. This known method can furthermore be developed in that the article surrounded by the disinfectant is irradiated with microwaves. The disinfection operation is carried out in a closed and sealed disinfection chamber, an atomizing or nebulizing device for disinfectant being arranged within the disinfection chamber. A further development of this disinfection chamber resides in that in the latter a microwave device is provided and outside the disinfection chamber a control device with which firstly the atomizing device is switched on and then, after formation of a disinfection mist in the disinfection chamber, the microwave device is switched on.

In such a disinfection chamber, which may also be constructed in the form of a sterilization tunnel, a plurality of microwave generators being arranged at the walls of the tunnel in succession, there is however the possibility on introduction of the refuse directly into the chamber of germs escaping from said chamber or tunnel, for example on formation of a draught, i.e. the germs or bacteria to be killed may by chance not be kept sufficiently long in the chamber or in the tunnel and consequently a 100% sterilization and disinfection cannot be achieved with high certainty.

DE 37 10 156 A1 discloses an apparatus for treating infected refuse with the aid of microwaves. The known apparatus includes a microwave chamber into which containers are introduced which are filled with the infected refuse and are hermetically sealed with the aid of a cover. The containers consist of microwave-transmissive material and in the microwave chamber itself a means is provided for moving the containers during the radiation with microwaves. Said means may for example be a conveying belt or a turntable.

The containers themselves may have in their interior a further container for receiving liquid, in particular water.

DE 35 05 571 C2 discloses an apparatus for the disinfection and sterilization of mattresses or the like with the aid of microwaves which comprises a microwave chamber for receiving the mattresses and at least one microwave transmitter for irradiating the moistened mattresses. The essence of this known apparatus resides in that the microwave chamber sealed all round has microwave-transmissive windows through which the microwaves are irradiated into the microwave chamber, that within the microwave chamber a microwave-transmissive mattress chamber is accommodated and that the microwave chamber and mattress chamber communicate with each other, the microwave chamber being formed jointly with the mattress chamber as lock and lock doors being provided on both sides of the mattress chamber.

For the disposal of infectious hospital waste and refuse a number of regulations exist and the observance thereof is supervised by the Federal Ministry of Health, who has also issued a decree in this respect. The basic idea is that in the disposal of infectious hospital refuse no contamination of the environment must occur.

In the microwave treatment of infectious hospital refuse, however, difficulties are encountered in conjunction with the fixedly sealed containers in so far as water must be introduced into the plastic container to permit a heating in the first place of the hospital refuse, which itself is relatively dry. It would for example also be possible to add water in the form of sealed plastic bags which the operator concerned also introduces into the plastic containers after the filling of the latter. However, from the safety point of view such a solution would not be acceptable because it cannot then be ensured that the operator might not occasionally forget to add a water container to the plastic container and that then the heating and sterilization of the hospital refuse would not be possible.

Even in cases where in the containers regions are provided beforehand in which water is kept which is liberated during the microwave treatment so that the refuse in the interior of the container is wetted with water the certainty is still not adequate because the respective operator might just forget to check whether a container used does in fact still contain an undamaged water reservoir.

It must therefore be ensured that irrespective of the attention of the operator the water always reliably enters the containers concerned.

A further problem in heating the infectious hospital refuse in plastic container resides in that the heating causes an excess pressure which might cause the container to burst.

SUMMARY OF THE INVENTION

Therefore the invention has as its object to provide a method and apparatus for the sterilization of refuse wherein the above-mentioned disadvantages do not occur.

More particularly, it is intended to provide a method and an apparatus for the sterilization of refuse, in particular hospital waste, of the type set forth in which the sterilization can be carried out with very great reliability and in particular it is always ensured that irrespective of the attention of an operator water always reaches the refuse container concerned.

Therefore the invention proposes a method and an apparatus for sterilizing refuse, in particular hospital refuse, using a plurality of disposable refuse containers which after loading with refuse are hermetically sealed by a cover and then introduced preferably severally into a sterilization tunnel and thereafter irradiated with microwaves, water or a disinfectant being introduced into the refuse of the refuse containers either before or during the microwave irradiation and the refuse container or containers then being discharged at a discharge end from the sterilization tunnel, wherein a) the refuse containers charged with refuse and hermetically sealed with a cover are brought onto a preparatory conveyor belt which is arranged in a lock chamber of the sterilization tunnel.

b) the lock chamber is then hermetically sealed at the introduction end, c) a lock door within the sterilization tunnel is opened and the refuse containers are brought from the preparatory conveyor belt onto a main conveyor belt within a sterilization chamber, d) the sterilization chamber is then hermetically sealed and via injection needles arranged movably in the sterilization chamber water or disinfectant is injected into each individual refuse container and e) after the microwave treatment all the refuse containers present in the sterilization chamber are discharged from the sterilization chamber at the discharge end with the aid of the main conveyor belt, the lock door being kept hermetically sealed.

The method according to the present invention can be carried out whilst ensuring high safety as regards contamination of the immediate environment of the sterilization apparatus and it is also always ensured that water or a disinfectant is present in the interior of the refuse containers.

The invention may be subjected to an advantageous further development in that the injection needles in the sterilization chamber are lowered from above downwardly onto the respective refuse containers to pierce the respective cover of the refuse containers.

It is however also possible to move the injection needles in the sterilization chamber from the side towards the refuse containers to pierce the refuse containers laterally.

To prevent emergence of pathogenic germs from the interior of the respective refuse container with great certainty the injection needles are held in position in their piercing state during the microwave treatment. An advantageous further development of the invention resides further in that more than one injection needle is inserted per refuse container. It is then possible to use one of the injection needles for introducing water or a disinfectant into the refuse container while a second needle is employed to carry away air or any gases within the refuse container to prevent formation of excess pressure within the refuse container. The extracted gas here can be sent via a sterilization cycle and then either discharged to the atmosphere or introduced into the sterilization chamber.

Furthermore, it is also possible to use at least one of the injection needles for injecting preferably heated water vapour into the refuse container. The gas extracted from the respective refuse container can be conducted via a filter, a heating region and/or a microwave radiation region to sterilize it as well.

To effectively prevent the escape of germs from the sterilization chamber and from the lock chamber as well, the lock door between the lock chamber and the sterilization chamber is hermetically locked when the discharge door of the sterilization chamber or the introduction door of the lock chamber is opened and furthermore the lock door is unlocked only when the discharge door of the sterilization chamber is closed and the introduction door of the lock chamber is closed.

The invention further relates to an apparatus for carrying out the method according to the invention which includes a sterilization channel having a sterilization chamber with an introduction end and a discharge end and a conveyor belt.

The invention further relates to an apparatus for sterilizing refuse, in particular hospital refuse, comprising a plurality of refuse containers which are sealable by a cover, pierceable by an injection needle and are suitable for the sterilization of refuse contained in them in a microwave sterilization tunnel which includes at least one conveyor path for simultaneous conveying of a plurality of consecutively arranged refuse containers and which has an injection means for injecting water or a disinfectant preferably simultaneously in a series of refuse containers.

According to the invention, this apparatus for the sterilization of refuse, in particular hospital refuse, is constructed in such a manner that it can be made in particularly compact design and it is always ensured that the piercing of the respective injection needle into the container takes place at an exactly defined desired pierce point in order to achieve a greater certainty in the sealing of the refuse container.

According to this embodiment at least one conveyor path is formed by a roller conveyor belt which is downwardly inclined from the introduction end to the discharge end of the sterilization tunnel so that the refuse containers placed on the roller conveyor path or suspended thereon due to their own weight are thereby conveyed in the direction towards the discharge end of the sterilization tunnel.

The refuse containers are each provided in the vicinity of their upper side with an encircling flange with the aid of which the refuse containers can be placed on or carried by the at least one roller conveyor path. Finally, the refuse containers are each equipped with a desired piercing point which consists of a wall portion sealing the pierce of an injection needle.

To achieve high efficiency in the sterilization of refuse the invention can undergo an advantageous further development in that in the sterilization tunnel two roller conveyor paths are arranged extending parallel and adjacent each other.

This latter step does not increase the overall length of the sterilization tunnel and makes it possible to nevertheless achieve a compact short overall length.

Expediently, at the discharge end of the respective roller conveyor path a detachable stop is provided up to which the first refuse container introduced into the sterilization tunnel can roll. The inclination of the respective roller conveyor path is dimensioned here so that the refuse containers arranged in a row in the respective roller conveyor path due to their own weight roll in the direction towards the discharge end of the sterilization tunnel, the leading refuse container being supported at the detachable stop and the following refuse containers being supported at each other so that a continuous uninterrupted container row is thereby formed.

This latter feature gives inter alia the advantage that the refuse containers are positioned on the respective roller conveyor path exactly relatively to each other so that the insertion of the respective injection needles can be made at an exactly defined point of the container.

Furthermore, for further transport of the treated refuse containers a transverse conveyor belt may be arranged at the discharge end of the sterilization tunnel to convey the refuse containers discharged from the sterilization tunnel to a compressed refuse container.

To increase the safety a small lock chamber may also be arranged at the introduction end of the sterilization tunnel.

The sterilization tunnel itself may be arranged mobile and for example installed on a truck or truck trailer.

The refuse containers are advantageously substantially square or rectangular in plan view and have rounded corners. This largely eliminates any misalignment of the refuse containers when charging a sterilization tunnel.

The encircling flange of the respective refuse container comprises holes arranged at intervals apart through which locking tongues formed on the cover of the refuse container may be inserted to lock the cover to the encircling flange. The encircling flange thus has two different functions; firstly it serves to support and hold the refuse container on the respective roller conveyor path and secondly serves to obtain a reliable closure between cover and refuse container.

To achieve a particularly reliable seal between cover and container the cover comprises an encircling groove which receives the upper container edge and in which a sealing element is arranged for sealing the cover at the container edge. Said sealing element consists in preferred manner of an elastic material, for example rubber, so that the locking operation can thereby be carried out rapidly and easily.

In particular, the invention may be further subjected to an advantageous further development in that the wall portion defining the desired piercing point is formed on the cover of the refuse container and consists of a wedge-like tapering wall depression, the contact line of the wedge-like extending walls at the bottom of the depression forming the piercing point. The wall portions contacting each other at the bottom of the depression are integrally joined together so that said region is completely sealed and no gases at all can escape there from the interior of the refuse container. The wedge-like converging wall portions merge in advantageous manner into an extended wall extension which points towards the interior of the container. The wall extension may conveniently terminate in a thinned wall extension edge, thereby achieving a very specific sealing effect. For when an injection needle is inserted through the bottom of the depression and after introduction of water into the container said injection needle is withdrawn again the piercing point is effectively sealed again by the pressure gradually building up in the interior of the container, the force sealing the piercing point being the greater the higher the pressure in the interior of the container.

To ensure a particularly effective mixing of the water with the refuse within the respective refuse container, it is further possible to form in the bottom of the respective refuse container a depression serving as water reservoir.

To monitor the course of the sterilization operation it is further possible to connect each of the injection needles to a temperature and pressure measuring means. The pressure measuring means may for example be integrated into the conduit system of the water supply. The pressure measuring means may be provided centrally at the water distribution system, a water main conduit being provided from which the individual water supply conduits branch off to the injection needles.

Another particularly advantageous further development of the invention resides in that the injection needle itself consists of a temperature sensor or is formed as temperature sensor. In this latter embodiment the injection needle can therefore fulfill two different functions.

Another embodiment further resides in that in the cavity of the injection needle a temperature probe is displaceably arranged. In a temperature measurement said temperature probe can expediently be pushed out a few centimeters beyond the needle tip when the needle has pierced a container, to such an extent that the temperature can easily be measured but there is nevertheless no danger of the temperature probe encountering refuse and being damaged.

The cover and/or the container may expediently consist of polyethylene and polypropylene.

Particularly advantageous further developments and embodiments of the apparatus and means according to the invention are set forth in claims 11 to 45.

BRIEF DESCRIPTION OF THE DRAWINGS

Hereinafter the invention will be explained in detail with the aid of an example of embodiment with reference to the drawings, wherein.

DESCRIPTION OF THE PREFERRED EMBODIMENTS

Figure 1:
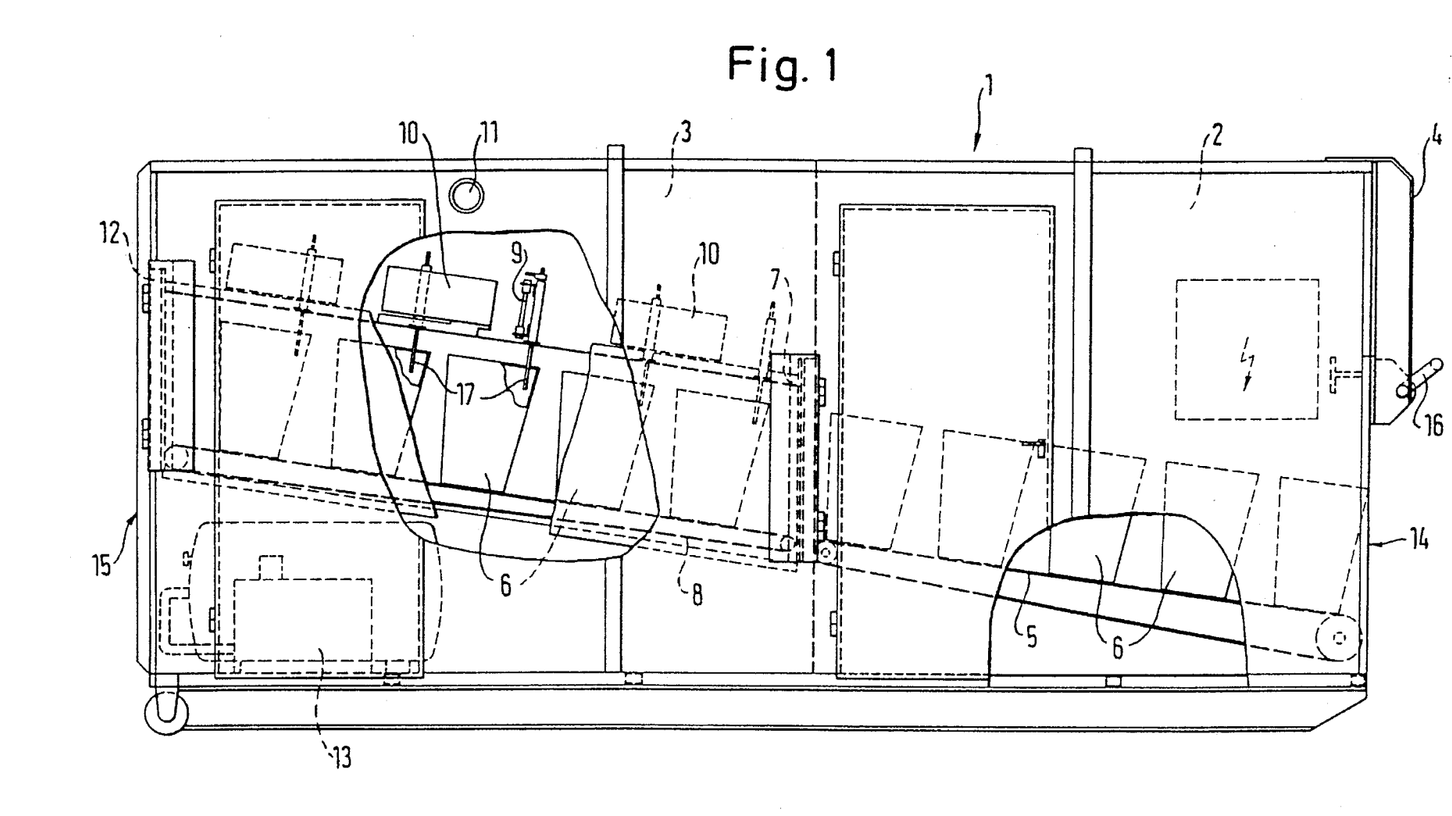
FIG. 1 shows in side elevation, partially broken away, a sterilization system in the form of a container for carrying out the method according to the invention.

FIG. 1 shows a side elevation, partially broken away, of a sterilization system in the form of a container which is denoted generally by 1. The container 1 is not arranged at a fixed location in the example of embodiment shown but is transportable and may therefore be set up for example on a truck or can even form a truck trailer itself. The system for sterilizing infectious hospital refuse and waste is accommodated in said container 1. The apparatus shown comprises a charging or introduction end 14 which is sealed by a pivotally arranged door 4. Said door 4 can be opened and closed by an operator with the aid of a grip 16. In the interior of the container, fundamentally two chambers are formed, a first lock chamber 2 and a following sterilizing chamber 3.

Within the lock chamber 2 a preparatory conveyor belt 5 is arranged which is dimensioned so that on said belt a plurality of plastic containers can be arranged in succession, for example five plastic containers a small distance apart in the conveying direction of the belt. Furthermore, the preparatory conveyor belt 5 has for example a width such that two or more plastic containers 6 may be arranged adjacent each other on the conveyor belt. In the example of embodiment illustrated the preparatory conveyor belt 5 runs inclined upwardly in the conveying direction so that the introduction end of the lock chamber 2 can be arranged lower than the discharge end. The lock chamber 2 is hermetically sealable with the aid of a lock door 7 with respect to the sterilization chamber 3 and a mechanism (not shown) is provided which effects that the lock door 7 always remains hermetically closed as long as either the door 4 at the introduction end 14 is open or the door 12 at the discharge end 15 of the sterilization chamber 3 is open. This ensures that for example during the microwave treatment gases within the sterilization chamber cannot penetrate into the lock chamber 2 and vice-versa.

Furthermore, a means may be provided by which it is ensured that after transfer of the refuse containers 6 from the preparatory conveyor belt 5 to a main conveyor belt within the sterilization chamber 3 the discharge door 12 remains closed until the sterilization operation is completely terminated.

As apparent from FIG. 1, the lock chamber 2 is followed by the sterilization chamber 3 and after opening the lock door 7 the charge of plastic containers 6 standing on the preparatory conveyor belt 5 can be transferred to the main conveyor 8.

When this charge of plastic conveyors 6 has then arrived at the interior of the sterilization chamber 3 the lock door 7, which may for example be a sliding door, is hermetically sealed and the discharge door 12 at the discharge end 15 of the sterilization chamber 3 is likewise hermetically sealed. With the aid of a mechanism 10 injection needles are then lowered from above the plastic containers 6 so that the injection needles 17 pierce the respective plastic container disposed below them in the cover region. Water or a disinfectant can then be injected via the injection needles 17 into the interior of the respective container.

To prevent bursting of the respective plastic containers by the injection of water and disinfectant and due to the subsequent heating of the moistened infectious hospital refuse within the container 6, either for example hot water vapour can be introduced into the sterilization chamber 3 via a suitable means and an opening 11, so that in the interior of the sterilization chamber 3 a correspondingly high counter pressure builds up, or alternatively it is also possible to associate with the particular plastic container 6 a plurality of injection needles, i.e. for example the respective cover of a plastic container is pierced by two injection needles spaced a slight distance apart, one injection needle being provided for introducing water or the disinfectant into the respective container whilst the other needle serves to extract gases within the respective plastic container and sterilize them via a separate cycle (not shown). Said cycle may include suitable filter means, for example active carbon filters or the like, or may comprise sections at which the gas extracted via the needle is heated to a high temperature to ensure sterilization in that manner. The sterilized gas can then either be returned to the sterilization space 3 or otherwise destroyed or discharged into the atmosphere.

The injection needles inserted into the respective plastic containers remain in that state until the entire sterilization operation has been concluded. This prevents pathogenic germs being able to escape outwardly from the interior of the respective plastic containers via the injection needles. In addition, the injection needles also serve to keep the respective plastic container 6 in position.

During a sterilization operation the main conveyor belt 8 may be driven via a drive mechanism 13 so that the containers on the main conveyor belt 8 are moved to and fro. This reciprocating movement is carried out by the injection needles 17 and the associated means 10.

Finally, after the microwave treatment the injection needles 17 are withdrawn with the aid of a suitable drive means 9 from the respective cover portions and thereafter the discharge end 15 is opened via the door 12. The main conveyor belt 8 is then correspondingly driven to discharge the treated plastic containers from the system.

It should be pointed out at this point that the containers 6 are plastic containers which on the one hand are permeable to microwaves but on the other hand are also disposable containers which are disposed for example with the aid of a compressed refuse container which compresses them under 30 tonnes pressure with reduction of volume. The respective containers can be allowed to burst when this is done because of course now they contain only sterile refuse.

At the same time of course a new charge of 10 containers may be driven onto the preparatory conveyor belt into the lock chamber 2.

Figure 2:
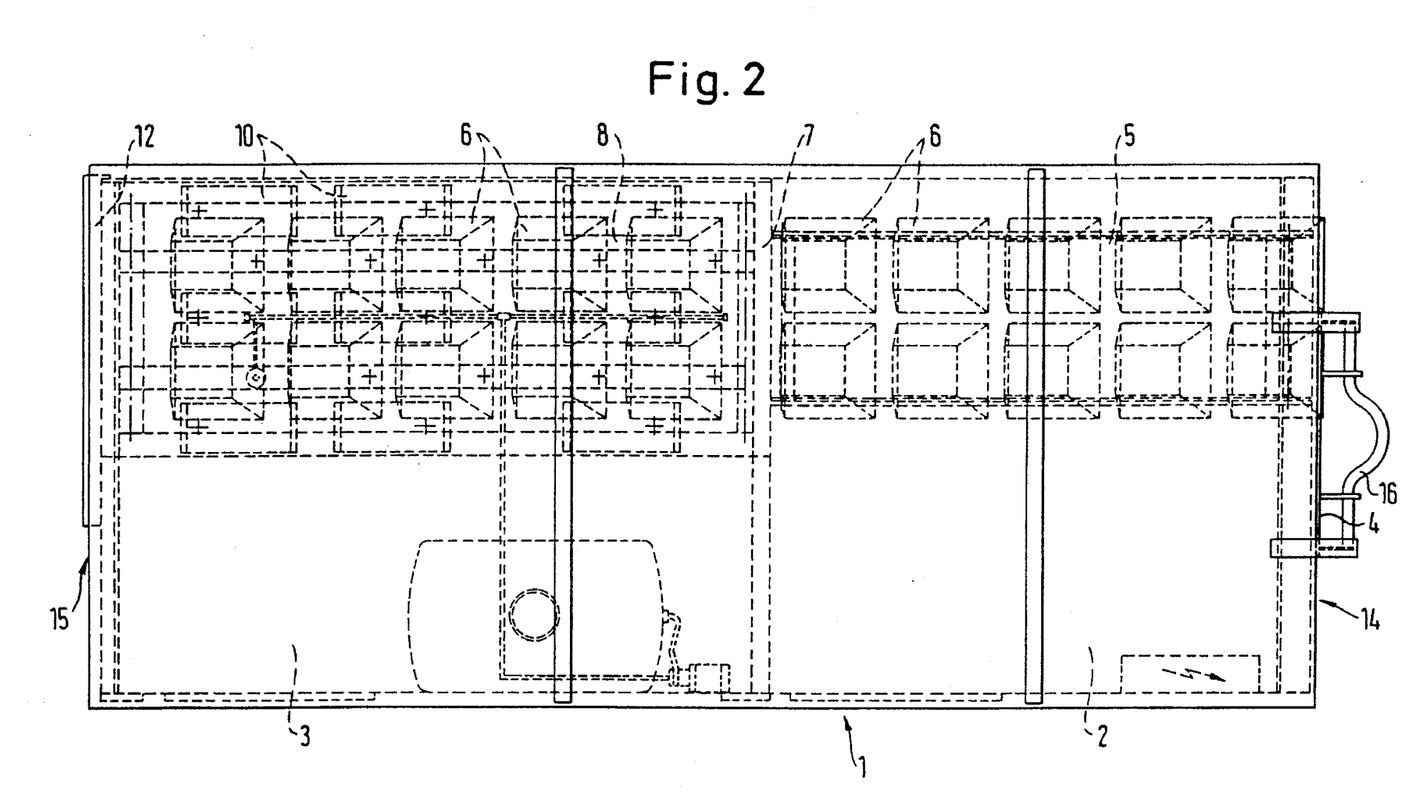
FIG. 2 is a plan view of the sterilization system of FIG. 1.

In a practical implementation of the system shown in FIGS. 1 and 2 the preparatory conveyor belt 5 is incrementally advanced in the charging operation until finally a total of ten refuse containers 6 is arranged on the preparatory conveyor belt 5. Thereafter, the introduction end 14 is sealed via the door 4 and the charge within the lock chamber 2 transferred to the sterilization chamber 3 in the manner outlined.

The present invention is not however restricted to the example of embodiment according to FIGS. 1 and 2.

For a person skilled in the art, a number of modifications and changes to this example of embodiment are possible. For example, it is possible to provide instead of the preparatory conveyor belt a turntable, this also applying to the main conveyor belt 8, and it is further possible to equip the system with a code reader which is able to read a specific code disposed on the containers 6 to determine whether the respective refuse container is a container suitable for the sterilization system and to reject unsuitable refuse containers, thereby further considerably increasing the safety and reliability.

It is further possible to make all the doors of the system as sliding doors and also the person skilled in the art will readily see that a locking mechanism for each of the doors can be constructed so that with specific door position combinations specific locking and/or unlocking states at other doors occur. This makes it possible to ensure in ever case that untreated refuse containers cannot leave the system without sterilization.

The invention is also clearly not restricted to the number of ten refuse containers making up a charge.

Furthermore, it is also possible for the injection needles not to pierce the plastic containers 6 or the cover elements from above downwardly but for the injection needles to pierce the respective containers laterally or in a horizontal direction.

The plastic containers may also be provided with an opening which permits gases at excess pressure on heating of the content of the plastic containers to escape to avoid bursting of the containers. Of course, into said opening a suitable filter, for example an active carbon filter, must be inserted which prevents germs and the like from being able to escape from the plastic container.

The plastic containers may also be made from a material expandable in particular under the action of heat. This makes it possible to take up an excess pressure occurring on heating of the content thereof in the microwave field without any danger of the plastic containers bursting or otherwise being damaged under the effect of said excess pressure.

Figure 3:
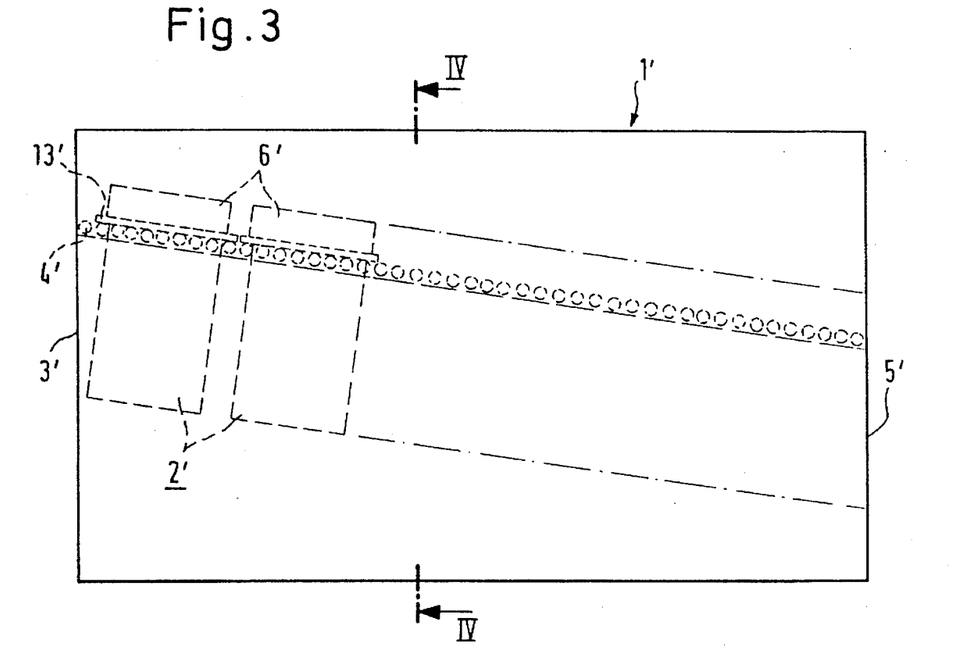
FIG. 3 is a schematic side elevation of a sterilization tunnel having the features according to the invention.

FIG. 3 shows schematically a further embodiment and a side elevation of a sterilization tunnel which is denoted generally by 1'. The sterilization tunnel 1' has an introduction or charging end 3' and a discharge end 5'. Between the introduction end 3' and the discharge end 5' a roller conveyor path 4' is arranged in such a manner that it extends slightly downwardly inclined from the introduction end to the discharge end.

In the example of embodiment shown, at the introduction end 3' a door (not shown) can be opened and the individual refuse containers 2' with covers 6' placed thereon can be placed on the roller conveyor paths 4' in such a manner that the refuse containers are held supported by rollers at lateral flanges 13' on opposing sides. The downwardly directed inclination of the roller conveyor belt is dimensioned so that the respective refuse conveyors due to their own weight are conveyed in the direction towards the discharge end 5', sliding over the rollers of the roller conveyor belt 4'. At the discharge end 5' a releasable stop, not shown, is provided against which the first refuse container placed on the roller conveyor path strikes.

According to another embodiment (not shown) the plastic container may be provided with a bag of flexible material which on heating of the content of the plastic container in the microwave field can bulge out into the space outside the plastic container and thus contribute to reducing the excess pressure in the plastic container.

Refuse containers then roll in the direction towards the discharge end 5' until they strike the respective preceding refuse container, thereby forming a continuous row of refuse containers between which no interruption or intermediate space is present so that each refuse container is positioned in an exact location which is always the same. After the door at the introduction end has then been hermetically sealed, with the aid of an injection means (not shown) including injection needles lowerable from above in the direction towards the respective cover of a refuse container water or a disinfectant is injected into each refuse container.

The injection needles can then either be withdrawn again from the respective refuse containers or held in the inserted state, whereupon a microwave sterilization apparatus (not shown) is activated. Due to the then resulting heating of the content of the refuse containers gases and water vapour develop so that an excess pressure arises in each refuse container. This excess pressure may be measured for example with the aid of a pressure measuring means which may expediently be integrated into the conduit system of the water supply.

In addition, a temperature measuring means may be provided for measuring the respective temperature occurring in the interior of the refuse containers. The temperature measuring means includes a temperature sensor and according to an advantageous further development of the invention the injection needle itself may be constructed as temperature sensor or according to an alternative embodiment in the cavity of the injection needle a displaceable temperature sensor may be arranged which can be moved out of the tip of the injection needle for measuring the temperature in the interior of the respective container.

After completion of the sterilization operation the inserted injection needles are then retracted again and the entire charge of the sterilization tunnel can then be discharged by opening a corresponding door at the discharge end 5'.

In the embodiment shown in FIG. 3 a plurality of roller conveyor paths may be provided extending parallel adjacent each other, that is for example two roller conveyor paths, so that in each case two refuse containers lying adjacent each other can be conveyed through the sterilization tunnel.

Figure 4:
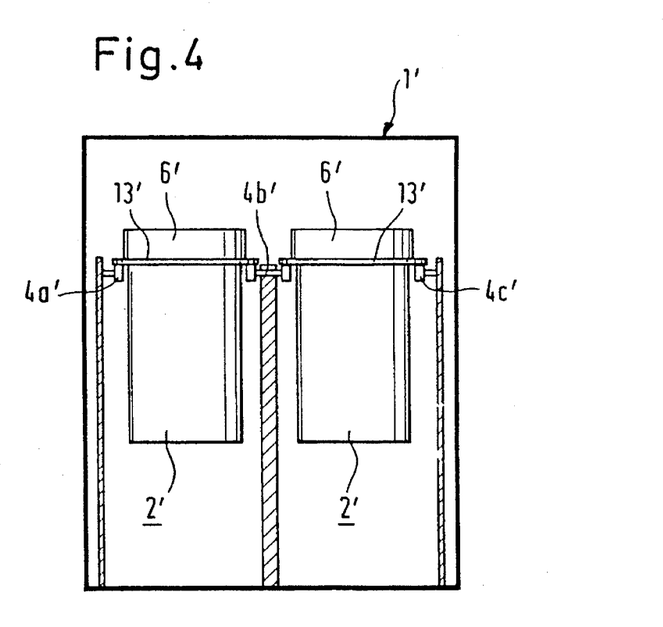
FIG. 4 is a sectional view of the sterilization tunnel along the line I—I of FIG. 3.

FIG. 4 shows a sectional view along the line I—I of FIG. 3.

As apparent from FIG. 4, a total of three roller conveyor paths 4a', 4b' and 4c' are arranged extending parallel adjacent each other. Consequently, a left refuse container 2' may be placed on the roller conveyor path 4a' and 4b' and a right refuse container on the roller conveyor path 4b' and 4c', said conveyors then being conveyed parallel through the sterilization tunnel 1'.

The sterilization tunnel may expediently be installed on a chassis, for example on a truck or a truck trailer, the construction shown being particularly suitable for this purpose because it can be made in comparatively short and compact manner.

Figure 5:
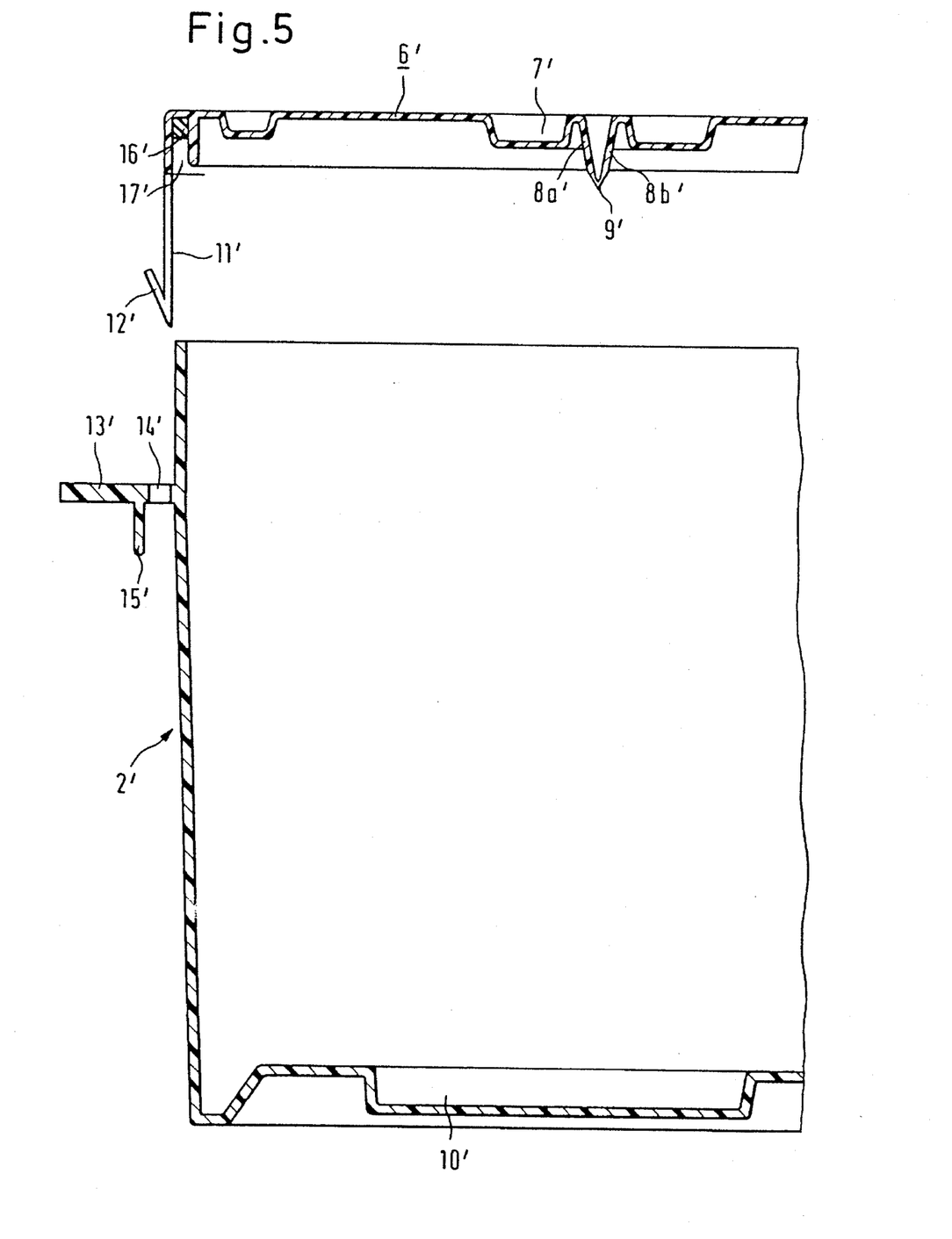
FIG. 5 is a schematic sectional view of part of the refuse container and of the associated cover.

FIG. 5 shows schematically a sectional view of the refuse container with cover. According to FIG. 5 a refuse container is equipped at its upper end region with an encircling flange 13' which extends in radial direction or horizontally. In the encircling flange slit-like openings 14' are provided at intervals and are associated with locking tongues 11', 12' of a cover 6'.

When the container 2' shown in FIG. 5 is filled with refuse it is hermetically sealed with the aid of the cover 6'. For this purpose the cover 6' need only be placed over the upper edge of the container 2' and pressed firmly onto the upper edge. The locking tongues 11', 12' then penetrate through the slit-like openings 14' in the encircling flange 13', pass through said slit-like openings 14' and finally reach an end position in which a hook-like projection 12' engages over a wall-like projection 15' projecting from the lower face of the encircling flange 13', thereby firmly locking the cover to the container 2'.

The cover 6' is further equipped with an encircling groove 17' into the bottom region of which a seal 16' is inserted, said seal consisting of an elastic material, for example rubber.

When the cover 6' is pressed onto the upper edge of the container 2' said seal 16' is elastically deformed so that the hook-like projection 12' can slip over the wall-like projection 15' to effect the locking. The container is then firmly sealed, in particular sealed tight as regards the medium.

In the central region of the cover 6' a depression 7' is further formed and in the central region thereof a wall portion corresponding to a desired piercing point is present. Said wall portion consists of two wedge-like tapering walls 8a' and 8b' which form a wedge-shaped depression.

At the bottom of said depression the two wall portions merge into each other and are integrally joined together. This lower common wall portion tapers downwardly as illustrated at 9'. This results in a relatively elastic thin wall region which forms the desired piercing point. Since the wall portions 8a' and 8b' extend in wedge manner, a certain guiding of the injection needle towards the bottom region 9' of the depression results and consequently the injection needle is guided exactly to the desired piercing point.

The wall extension of reduced wall thickness forms a sort of check valve, the mode of operation of this construction being as follows:

When an injection needle is inserted through the extended wall extension according to the reduced point 9' and thereafter withdrawn again, the wall portions 8a' and 8b' in the region of this extended wall extension are pressed together with gradually increasing internal pressure. As a result, the opening corresponding to the piercing point is automatically sealed, the sealing being the more effective the higher the internal pressure in the container.

According to an alternative embodiment it is possible to make the wall portions 8a' and 8b' from a relatively soft resilient material, thereby favouring the closure of the piercing opening.

The container 2' may further comprise in its bottom region a depression 10' which can serve as additional water reservoir. On heating of the refuse contained in the hermetically sealed container and of the injected water the water in the water reservoir 10' is necessarily also heated and evaporates so that the refuse in the interior of the container is intensively mixed with moisture, thereby increasing the sterilization effect.

Since the individual refuse containers are arranged in the sterilization tunnel in such a manner that they bear on each other in the movement direction, for each refuse container an exact positioning results within the sterilization tunnel so that an exact introduction of the injection needles into the region between the wall portions 8a' and 8b' is ensured.

The heating of the refuse in the interior of the refuse container can be increased up to a temperature of 150° C., although a temperature of 120° C. is preferred.

Both the cover 6' and the container 2' may be made from polyethylene or polypropylene.

Each refuse container has substantially square shape when viewed from above so that the exact positioning of the respective container in the sterilization tunnel does not present any problems at all.

For the person skilled in the art a number of modifications may readily be made to the examples of embodiment explained without thereby leaving the scope of the present invention. Thus, it is for example possible to regulate the microwave energy in dependence upon the measurement result on measuring the pressure in the interior of the refuse container to maintain the temperature at a specific predetermined value or to maintain the pressure in the interior of the refuse container at a predetermined value or to disconnect the excitation of the microwave generator system (not shown) on reaching predetermined pressure and temperature values.

It is further also possible to make the refuse containers not square but elongated or rectangular and with this configuration as well a high certainty in the positioning of the refuse containers in the interior of the sterilization tunnel is achieved because the refuse containers can then be placed on the roller conveyor paths and introduced only in a quite specific angular position.

I claim:

1. An apparatus for the sterilization of refuse, in particular hospital refuse, which is contained inside of a refuse container which is hermetically sealable by a cover and pierceable by an injection needle to inject water or a disinfectant into said refuse container to be evaporated, said apparatus comprises an injection means including at least one of said injection needles to be injected into said container and a device for moving said at least one of said injection means toward said refuse container for piercing the refuse container, wherein a pressure measuring means is connected with said at least one injection needles and can be brought into contact with the interior of said refuse container, a temperature measuring means which can be brought into contact with the interior of said container by means of said at least one injection needles.

2. An apparatus according to claim 1, wherein a gas extracting means is arranged for extracting the internal atmosphere of said refuse container at least partially out of the interior thereof.

3. An apparatus according to claim 1, wherein said apparatus is arranged in a sterilization chamber.

4. An apparatus according to claim 3, wherein said apparatus and said sterilization chamber are located in a lock chamber which is hermetically sealable via a lock door with respect to the sterilization chamber.

5. An apparatus according to claim 1, comprising a means to introduce heated water vapor into the sterilization chamber under pressure.

6. An apparatus according to claim 1, comprising a means for generating a partial vacuum in the sterilization chamber.

7. An apparatus according to claim 3, wherein the sterilization chamber is formed in a transportable container.

8. An apparatus according to claim 4, wherein the lock chamber and the sterilization chamber are formed in a transportable container.

9. An apparatus according to claim 1, comprising a code arranged on the refuse container and a code reading device at the introduction end of the lock chamber to recognize refuse containers suitable for the sterilization plant and to reject unsuitable refuse containers.

10. An apparatus according to claim 1, wherein injection needles are employed having a plurality of passages with openings which preferably lie spaced apart from each other to let liquids and/or gases flow in and/or out of the refuse containers.

11. An apparatus according to claim 1, wherein a plurality of refuse containers for the sterilization are movable into a microwave sterilization tunnel for evaporating said inject water or said disinfectant, which includes at least one conveyor means for the simultaneous conveyance of a plurality of consecutively arranged refuse containers, and said injection means being preferably formed for simultaneously injecting said injecting water or said disinfectant into a series of refuse containers, wherein the refuse containers are each provided with an encircling flange and the refuse containers are equipped with a wall portion establishing the desired piercing point and assisting the sealing of the pierce of an injection needle.

12. An arrangement according to claim 11, wherein the conveyor means is formed by a conveyor which is inclined downwardly from the introduction end to the discharge end of the sterilization tunnel.

13. An arrangement according to claim 11, wherein a lock chamber is arranged at the introduction end of the sterilization tunnel.

14. An apparatus according to claim 11, wherein the sterilization tunnel is arranged to be mobile and installed in a truck or truck trailer.

15. An arrangement according to claim 11, wherein the refuse container is substantially square or rectangular in plan view and has rounded corners.

16. An arrangement according to claim 11, wherein the encircling flange of the respective refuse container comprises holes arranged at intervals apart through which locking tongues formed on the cover of the refuse container may be inserted to lock the cover to the encircling flange.

17. An arrangement according to claim 16, wherein the cover comprises an encircling groove which receives the upper container edge and in which a sealing element is arranged for sealing the cover at the container.

18. An arrangement according to claim 11, wherein the wall portion determining the desired piercing point is formed on the cover of the refuse container and consists of a wedge-like tapering wall depression, the contact line of the wedge-like extending walls at the bottom of the depression forming the piercing point.

19. An arrangement according to claim 18, wherein the wedge-like converging wall portions merge into a wall extension extended towards the interior of the container.

20. An arrangement according to claim 19, wherein the wall extension terminates in a thinned wall extension edge.

21. An arrangement according to claim 18, wherein the wall portion determining the desired piercing point is formed in a depression of the cover or of the side wall of the container.

22. An arrangement according to claim 15, wherein in the bottom of the refuse container a depression serving as water reservoir is formed.

23. An arrangement according to claim 11, comprising a pressure and temperature measuring means connected with the injection needle.

24. An arrangement according to claim 23, wherein the pressure measuring means is integrated into the conduit system of the water supply.

25. An arrangement according to claim 24, wherein the pressure measuring means is provided centrally at the water distribution system a water main conduit being provided from which the individual water supply conduits branch off to the injection needles.

26. An arrangement according to claim 22, wherein the injection needle itself consists of a temperature sensor.

27. An arrangement according to claim 23, wherein in the cavity of the injection needle a temperature probe is displaceably arranged.

28. An arrangement according to claim 15, wherein the cover and/or the container consist of polyethylene and/or polypropylene.

* * * * *